United States Patent [19]

Sheffield

[11] Patent Number: 5,356,217
[45] Date of Patent: Oct. 18, 1994

[54] ENTHALPIMETRIC ANALYZER AND METHOD OF USE

[75] Inventor: Gary S. Sheffield, Westerville, Ohio

[73] Assignee: The Edward Orton, Jr. Ceramic Foundation, Westerville, Ohio

[21] Appl. No.: 986,099

[22] Filed: Dec. 4, 1992

[51] Int. Cl.$^5$ .................... G01N 25/00; G01N 25/02
[52] U.S. Cl. ........................................ 374/45; 374/25; 364/556; 364/577
[58] Field of Search ........................ 374/10, 11, 12, 13, 374/25, 45; 364/556, 557, 577

[56] References Cited

U.S. PATENT DOCUMENTS

| | | | |
|---|---|---|---|
| 2,794,844 | 6/1957 | Corneil . | |
| 3,316,750 | 5/1967 | Takeya et al. | 374/12 |
| 3,332,285 | 7/1967 | Cook . | |
| 3,360,993 | 1/1968 | MacMillan | 374/10 |
| 3,504,522 | 4/1970 | Jasik et al. . | |
| 3,737,762 | 6/1973 | Fletcher et al. | 374/13 |
| 3,843,872 | 10/1974 | Shimomura . | |
| 4,154,085 | 5/1979 | Hentze | 374/10 |
| 4,466,749 | 8/1984 | Cunningham et al. | 374/134 |
| 4,480,930 | 11/1984 | DeZubay et al. | 374/134 |
| 4,606,649 | 8/1986 | Mikhail | 374/10 |
| 4,812,051 | 3/1989 | Paulik et al. | 374/10 |
| 5,163,753 | 11/1992 | Whiting et al. | 374/10 |
| 5,211,477 | 5/1993 | Li | 374/10 |

FOREIGN PATENT DOCUMENTS 2161924  6/1973  Fed. Rep. of Germany ........ 374/12

OTHER PUBLICATIONS

Muller, R. H., "Differential Thermal Analysis," Analytical Chemistry, vol. 35, No. 4, (Apr. 1963).
Skinner, K., "A Differential Thermal Analysis Apparatus for Temperatures up to 1575° C.," Naval Research Laboratory NRL Report #4942 (May 24, 1957).
Sheffield "Quantitative Measurement of Crystalline Silica by Thermal Analysis" Crystalline Silica Symposium Cambridge, Mass., Aug. 20–21, 1992.
Chung, "Synthesis and Anaylsis of Crystalline Silica" Environ. Sci. Technol. vol. 16, No. 11, pp. 796–799 (1982).
Ibrahim, Kabish and Sallam "Quantitative Determination of Cristobalite by Thermal Methods" Thermochimica Acta 45 (1981) pp. 167–176.
Sheffield, Hare, McGaughey "Single Thermocouple Differential Thermal Analysis with Application Quantitative Low Level Detection". . . Thermochimica Acta, 32 (1979) pp. 45–52.
Schelz "The Detection of Quartz in Clay Minerals by Differential Thermal Analysis" Thermochemica Acta, 15 (1976) pp. 17–28.

(List continued on next page.)

*Primary Examiner*—Diego F. F. Gutierrez
*Attorney, Agent, or Firm*—Mueller and Smith

[57] ABSTRACT

An automated thermal analysis system and method for the detection and quantitative measurement of analytes having thermally-induced, energy events and associated enthalpy changes is described. The system and method are automated to simplify data acquisition and analysis and to enhance sensitivity. The temperature of at least one sample containing at least one analyte having a thermally-induced, energy event is measured upon heating or cooling through the temperature range of the energy event of the analyte to derive a time-temperature curve corresponding to the enthalpy change of the analyte. From the time-temperature curve and a preselected reference parameter derived therefrom in the vicinity of the energy event region of the analyte, analyte concentration in the sample may be derived from a calibration curve correlating the preselected reference parameter to a normalized sample weight or volume. Alternatively, analyte concentration may be derived by a residual analysis of the time-temperature data or by fitting an $n^{th}$ order polynomial to data obtained in the energy event region and subtracting therefrom a reference curve obtained by interpolation of pre- and post-event data or by running an inert or analyte-free sample in a separate run.

43 Claims, 10 Drawing Sheets

OTHER PUBLICATIONS

Anderson "Free Silica Analysis of Environmental Samples a Critical Literaure Review" American Industrial Hygiene Assoc. Journal Oct. 1975 pp. 767–778.

Rowse and Jepson "The Determination of Quartz in Clay Minerals" Journal of Thermal Analysis vol. 4, pp. 169–175 (1972).

el Kolali and Gad, "On the Determinaton of Free Silica in Ceramic Raw Materials" J. Appl. Chem. Biotechnol. vol. 21, pp. 343–346 (Dec. 1971).

Mackenzie, Differential Thermal Analysis vol. 1, Ch. 17, pp. 477–495 (1970).

White and Grinshaw "The Determination of Crystalline Quartz by Differential Thermal Analysis: A Modification of Technique" Trans. Brit. Cer. Soc. 69, pp. 175–176 (1970).

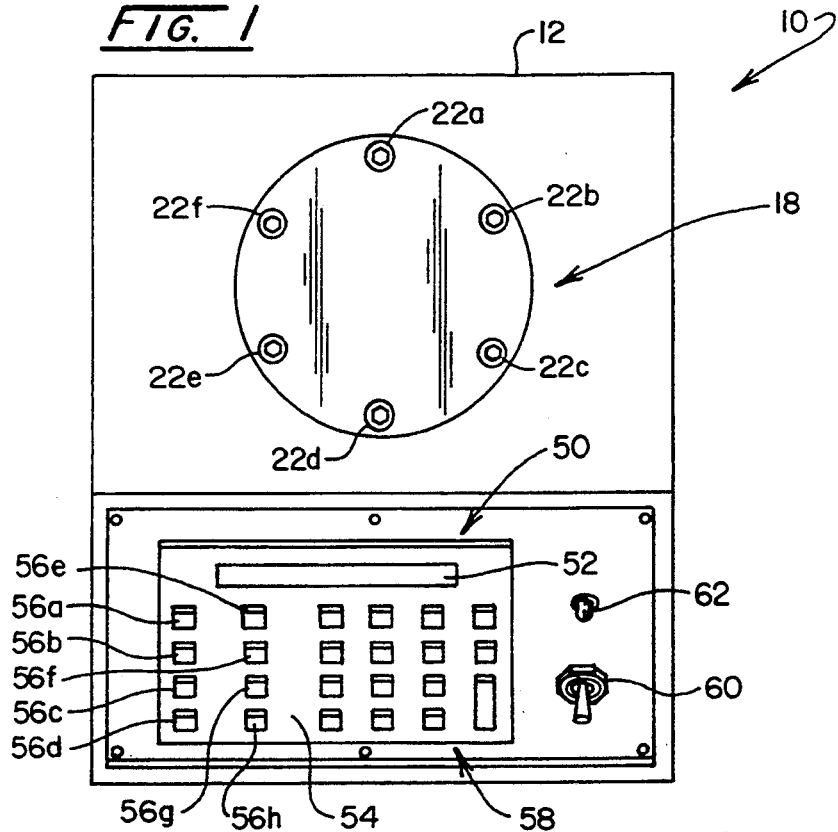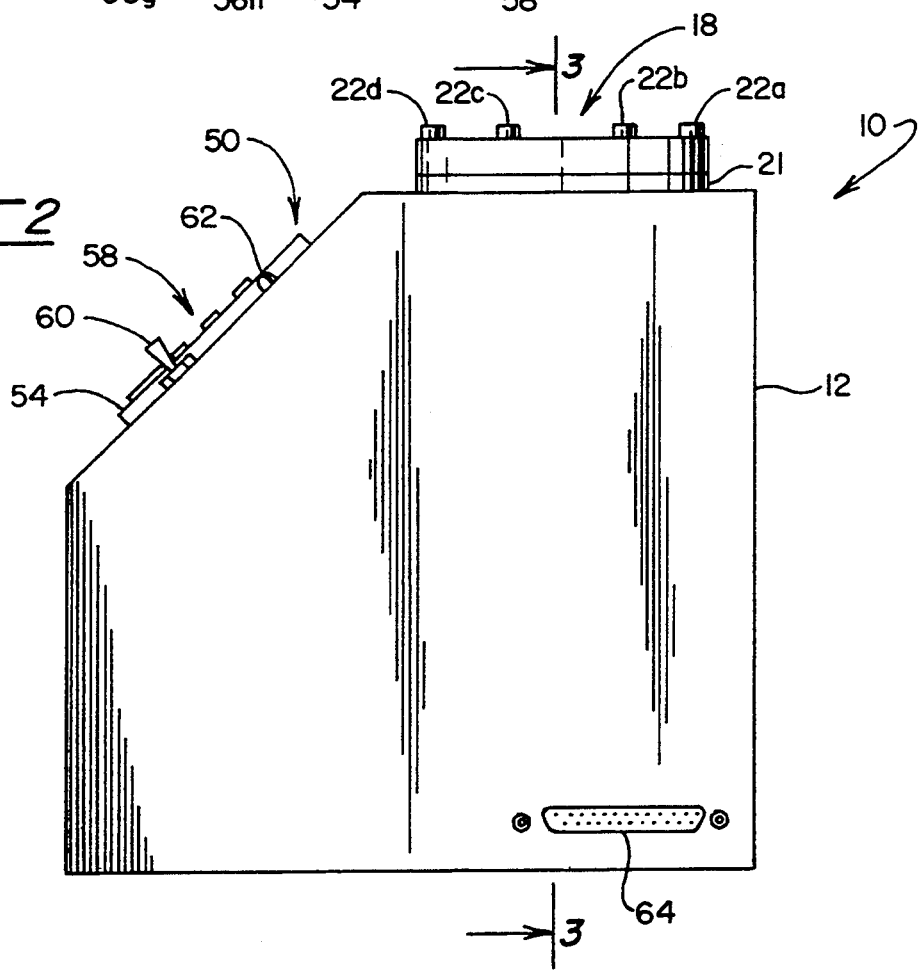

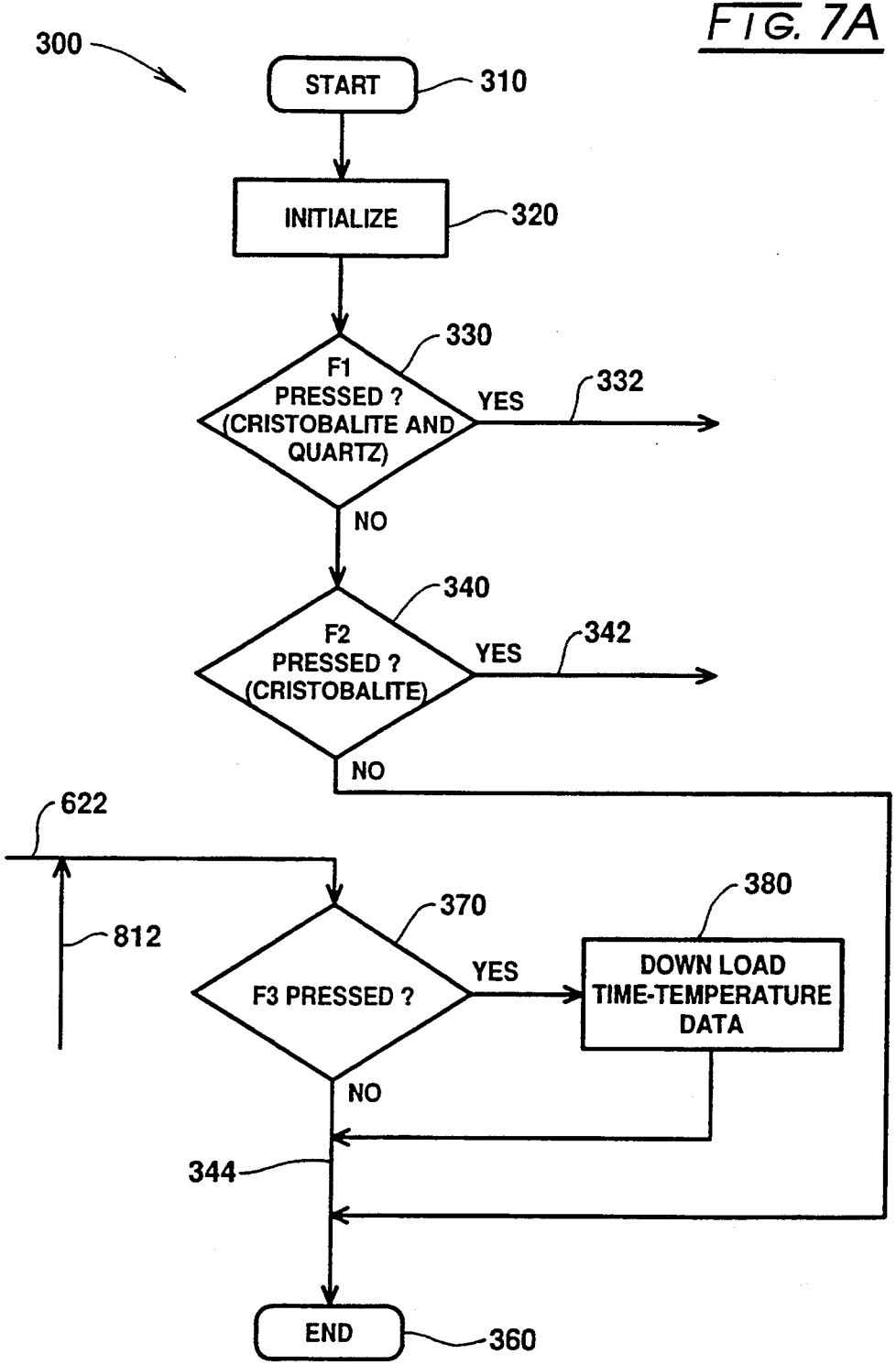

FIG. 7B
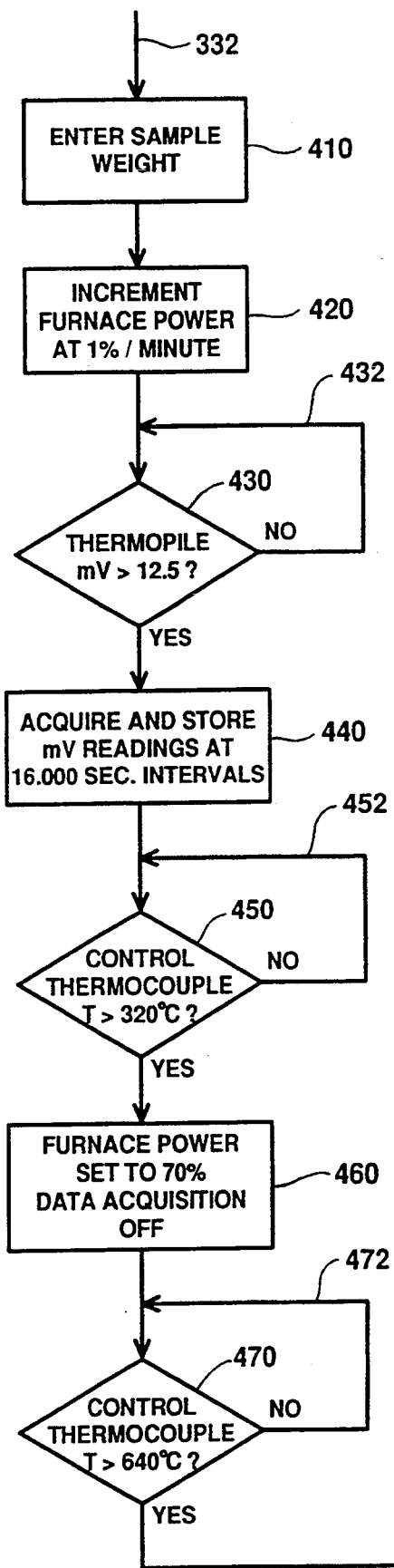
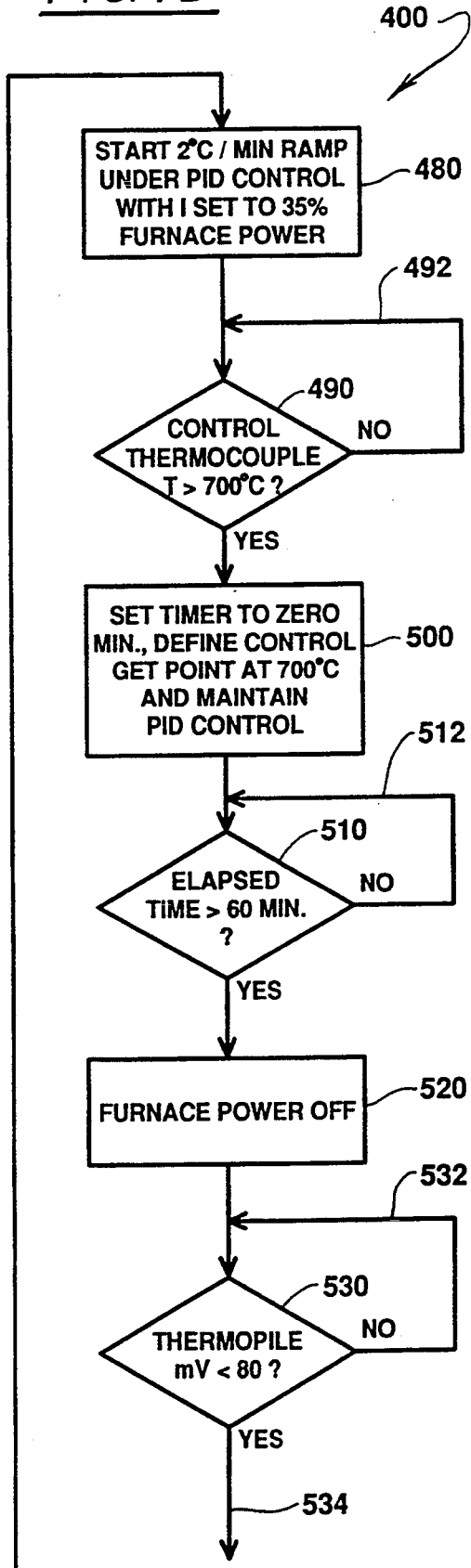

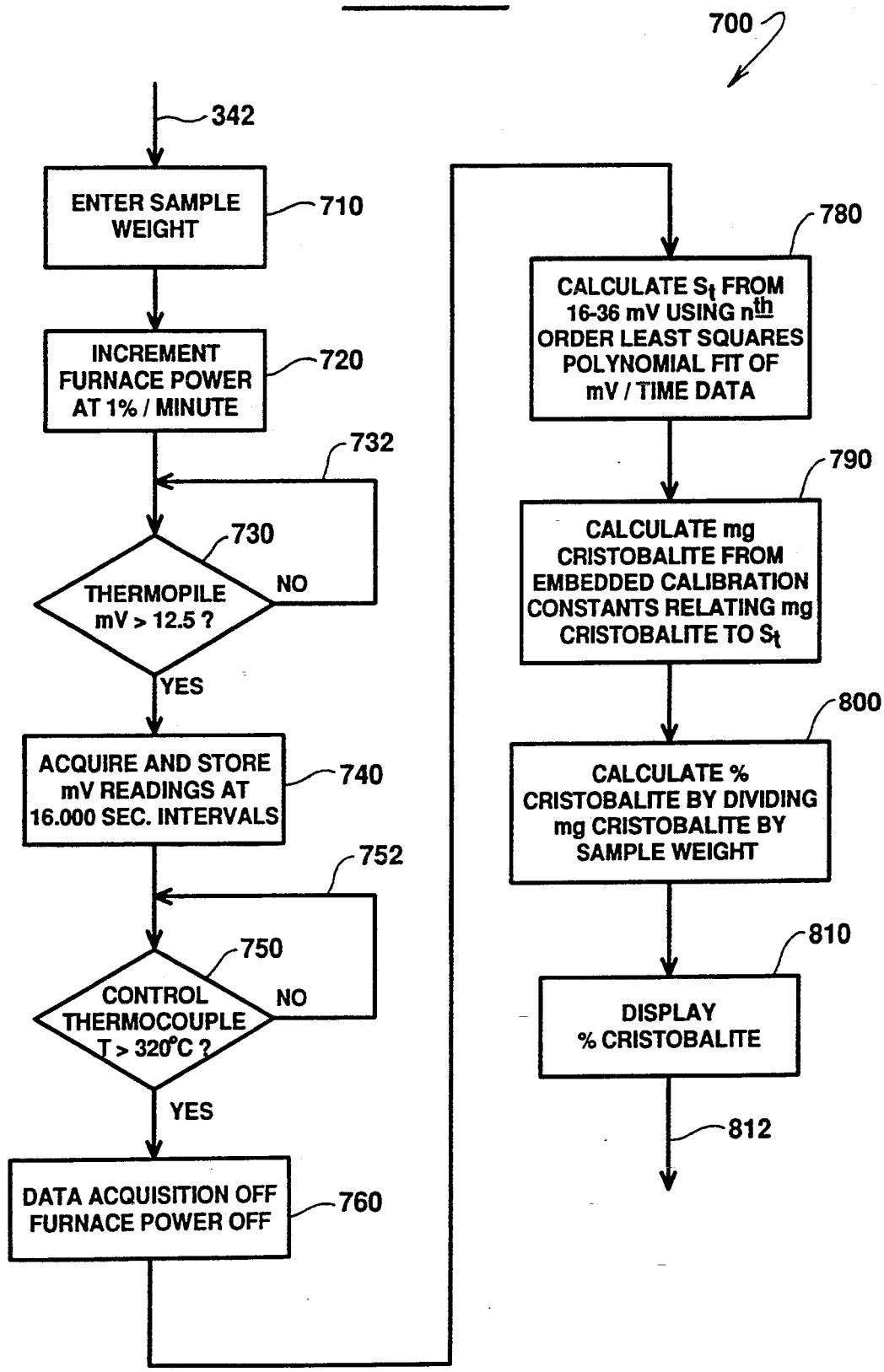

ENTHALPIMETRIC ANALYZER AND METHOD OF USE

BACKGROUND OF THE INVENTION

The present invention relates to a thermal analysis system and method for detection and quantitative measurement of an analyte undergoing a thermally-induced, energy event having an associated enthalpy change. Thermal analysis generally has been characterized by a two-thermocouple system. The present invention, in employing a single thermocouple, a thermopile, or other temperature sensor and in providing for automated data acquisition, simplifies analysis and provides for increased sensitivity.

Thermal analysis is generally characterized as a quantitative analytical method that is used, for example, to thermodynamically detect the concentration of an analyte in a sample. For many compounds, the normal room temperature phase may not be stable over the entire solid or liquid state temperature range. As the temperature of such compounds is increased from room temperature, a competing phase may have lower free energy and the compound will accordingly experience a phase change. Concomitant with or independent of the phase change, the analyte may also experience a decomposition or a chemical reaction with another compound. The phase change or chemical reaction produces an endothermic or exothermic enthalpy change, i.e., a liberation or absorption of heat, which can be measured and from which the concentration of the compound in the sample can be determined.

Thermal analysis traditionally has been characterized by a differential method employing two thermocouples joined in series. A first thermocouple is disposed in thermal adjacency with a first sample containing an analyte whose concentration is to be determined. A second thermocouple is disposed in thermal adjacency with an second, inert sample substantially free of the compound contained in the first sample. The samples are then placed in a furnace and the temperatures of the samples are raised to beyond the phase transition temperature of the compound in first sample. The temperature or energy difference between the samples is measured upon heating and/or cooling to derive a thermal analysis curve having a peak representative of the enthalpy change of the analyte in the first sample. From peak height or peak area, the concentration of the analyte in the first sample can be determined.

Two-thermocouple differential thermal analysis, however, is inherently disadvantaged in its sensitivity to minute temperature changes in the sample. As a result of differences in heat capacity, heat leakage, density and thermal conductivity between the sample and the reference material, considerable baseline drift can occur and cause significant interpretation problems, particularly when quantitative results are required.

To remedy the perceived limitations in the two-thermocouple thermal analysis method, investigators have proposed a single-thermocouple thermal analysis system. Sheffield et al. have described a single-thermocouple thermal analysis method wherein the sample itself is used as the reference. See "Single Thermocouple Differential Thermal Analysis With Application to Quantitative Low Level Detection of Free Crystalline Quartz," *Thermochimica Acta*, 32 (1979) 45–52. The method disclosed entails disposing a thermocouple connected to a digital multimeter in thermal adjacency with a sample contained in a furnace. A reference junction isothermally maintained in a reference bath is series coupled to the sample thermocouple. The sample is heated to a specified temperature, and voltage readings are manually recorded as a function of time as the sample experiences Newtonian cooling. Voltage-time data outside of the transition region is fitted to a least squares polynomial and the residuals in the transition region are summed at discrete data points to yield a value proportional to the transition enthalpy.

MacMillan, U.S. Pat. No. 3,360,993, describes a single-thermocouple technique for determining the transition temperature of compounds by measuring the difference in EMF (V) between a single thermocouple located in a sample and an ice-point-reference thermocouple. The difference derived then is differentiated with respect to time (t) by an analog servo system having an output proportional to $dV/dt$ which is automatically recorded as a function of sample temperature.

Although the single-thermocouple techniques described in the prior art do afford some advantages over the traditional two-thermocouple method, there nevertheless remains a need for an automated thermal analysis system with increased sensitivity to detect and quantify, for example, minute quantities of quartz, cristobalite and the like contained in ceramic or other materials. Such a need has been spurred by evidence that airborne particles of crystalline silica, e.g., quartz, cristobalite, tridymite, and the like, pose respiratory and possible carcinogenic health hazards even at low concentrations. In 1987, the International Agency for Research on Cancer (IARC) declared crystalline silica a possible human carcinogen, i.e., category 2A. See IARC Monographs on the Evaluation of the Carcinogenic Risk of Chemical to Humans, Vol. 42, Silica and Some Silicates, World Health Organization, International Agency for Research on Cancer, Lyons, France, 1987. In the U.S., the Occupational Safety and Health Administration (OSHA) enforces a permissible exposure limit (PEL) of 0.1 mg/m$^3$ and regulates substances containing $\geq 0.1\%$ crystalline silica. See U.S. Occupational Safety and Health Administration Toxic and Hazardous Substances, 29 C.F.R. 1910, 1200, U.S. Government Printing Office, Washington, D.C., 1989.

Detection of crystalline silica at the 0.1% regulatory threshold has, however, challenged industrial mineral producers, mineral importers and exporters, analytical equipment manufacturers, and analysts. X-ray diffraction traditionally has been the analytical method of choice for quantitative determination of mineral phases. However, most X-ray diffraction instruments, except those of the most recent generation, have lacked the sensitivity to achieve detection limits of 0.1% or less. Moreover, X-ray diffraction is disadvantaged in that many of the common rock forming minerals, i.e., feldspar, kaolin, barite, have diffraction lines that interfere with one or more of the major quartz diffraction lines. X-ray diffraction is also matrix dependent, making it difficult to develop a single analytical method that can be applied to a variety of silica-containing materials. In addition, X-ray results can be influenced by the non-crystalline short range order that can occur regularly in SiO$_2$-based materials and may, accordingly, indicate crystallinity in samples even where no phase transitions occur.

Moreover, even at levels above the 0.1% regulatory threshold, detection of crystalline silica and the like is of commercial importance in that a volume change also accompanies the phase transition. For example, length changes of about 0.2% can occur when quartz undergoes its transition. For cristobalite, the length change can be as much as 1.1%. Such volumetric changes can produce considerable stresses within an article of manufacture which, in turn, can result in cracking and consequent premature failure of the article. Consequently, it may be seen that there has existed and remains a need for an automated system capable of quantitatively measuring amounts of crystalline silica and the like.

BROAD STATEMENT OF THE INVENTION

The present invention is addressed to an automated thermal analysis system and method for the quantitative measurement and detection of an analyte, such as crystalline silica or the like, having a thermally-induced, energy event and an associated enthalpy change. The energy event may be a crystalline phase transition, a physical phase or state transition, or a compositional change effected by a reversible or decompositional chemical reaction. The temperature of at least one sample containing at least one analyte having such a thermally-induced, energy event is measured upon heating or cooling of the sample through the temperature range of the energy event to derive a time-temperature curve corresponding to the enthalpy change of the analyte. From the time-temperature curve, temperature or energy changes corresponding to the enthalpy change in the analyte and, accordingly, its concentration in the sample may be derived. By employing a single thermocouple, a thermopile, or another temperature sensor disposed in thermal adjacency with the sample and by employing automated data acquisition methods, the present invention simplifies enthalpimetric analysis, is free from the interference effects associated with X-ray diffraction, and provides for increased sensitivity in the detection and quantitative measurement of, for example, minerals such as crystalline silica and the like at concentrations from as high as 100% to below 0.1%. In this regard, the invention will be understood to differ from conventional differential thermal analysis in having only a single temperature sensor and, if necessary, an associated cold or reference junction to measure sample temperature rather than both a sample and an inert sample sensor, each of which having, if necessary, an associated cold junction, to measure the temperature differential between the sample and an inert reference sample.

The enthalpy change of an analyte and its concentration in a sample may be derived from a time-temperature curve derived from data acquired as the sample is heated or cooled through the temperature range of the energy event of the analyte. From the time-temperature curve and a preselected reference parameter derived therefrom in the vicinity of energy event of the analyte, analyte concentration in the sample may be derived from a calibration curve correlating the preselected reference parameter to a normalized sample weight or volume. Advantageously, the calibration curve may be embedded into firmware or the like to further automate data analysis. Alternatively, analyte concentration may be derived by a residual analysis of the time-temperature data or by fitting an $n^{th}$ order polynomial to data obtained in the energy event region and subtracting therefrom a reference curve obtained by interpolation of pre- and post-event data or by running an inert or analyte-free sample in a separate run.

It is, therefore, an object of the present invention to provide an automated system for determining the amount in at least one sample of at least one analyte having a thermally-induced, energy event and an associated enthalpy change. The system includes a closable chamber for receiving the sample and a heating arrangement disposed within the chamber in heat transfer adjacency with the sample. The heating arrangement is responsive to control signals submitted thereto for heating or cooling the sample at a preselected rate. The temperature of the sample is measured by a sensor arrangement which provides output signals having amplitudes corresponding to the temperature of the sample. A converter converts these output signals to digital signals for selective storage in a memory. A processor is provided to effect the selective storage of the digital signals as a function of time over a predetermined temperature range which includes the temperature range of the energy event of the analyte. The processor also retrieves the selectively stored digital signals from the memory and derives therefrom process signals proportional to the amount of the analyte in the sample. The process signals may be submitted to a perceptible arrangement for the display or publishing of the amount of the analyte in the sample as a quantity or as the exceeding of a preselected threshold level. For control of the processor, a manually-actuable data input arrangement is provided for deriving select function signals and operational parameter inputs to which the processor is responsive for deriving control signals and effecting the submittal thereof to the heating arrangement.

Another object of the invention is to provide an automated method for determining the amount in at least one sample of at least one analyte having a thermally-induced, energy event and an associated enthalpy change. The amount of the analyte in the sample may be displayed or published as a quantity or as the exceeding of a preselected threshold level. The method entails heating or cooling the sample at a preselected rate over a predetermined temperature range which includes the temperature range of the energy event of the analyte. The temperature of the sample is then sensed over the preselected temperature range and corresponding output signals are generated which are stored as a function of time in a provided memory. The selectively stored output signals are retrieved from the memory and the amount of the analyte in the sample is calculated therefrom. In one embodiment, the calculation is conducted by integrating the retrieved output signals over a first region defined by the intersection of a first curve corresponding to the selectively stored output signals in the vicinity of the energy event of the analyte and a select lower bound thereof. Also integrated is a second region defined by the intersection of a second curve and a select lower bound thereof corresponding to the thermal response as a function of time over the preselected temperature range of a preselected inert reference sample. The difference in area between the first and the second regions is determined and the amount of the analyte in the sample is displayed or otherwise published in correspondence with the difference in area. In another embodiment, the calculation is conducted by performing a least squares analysis on the selectively stored output signals which correspond to the pre- and post-event thermal response of the sample. A residual analysis is then performed on the selectively stored output signals. The amount of analyte in the sample is displayed or otherwise published in correspondence with the residual analysis. In yet another embodiment, the calculation is conducted by determining the value of a preselected reference parameter for the retrieved selectively stored output signals. Reference data corresponding to the preselected reference parameter is then interpolated to determine the amount of analyte corresponding to the value of the reference parameter for the retrieved selectively stored output signals. The amount of the analyte in the sample which corresponds to this value is then displayed or otherwise published.

The invention, accordingly, comprises the apparatus and method possessing the construction, combination of elements, arrangement of parts and steps which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 1 is a top elevational view of the analyzer system according to the invention.

FIG. 2 is a side elevational view of the analyzer shown in FIG. 1.

FIG. 7A is a flow diagram of the programmed operations of the analyzer according to the invention.

FIGS. 7B and 7C is a flow diagram of a cristobalite and quartz analysis subroutine for the programmed operations of the analyzer according to the invention.

FIG. 7D is a flow diagram of a cristobalite analysis subroutine for the programmed operations of the analyzer according to the invention.

The drawings will be described further in connection with the following Detailed Description of the Invention.

DETAILED DESCRIPTION OF THE INVENTION

Figure 3:
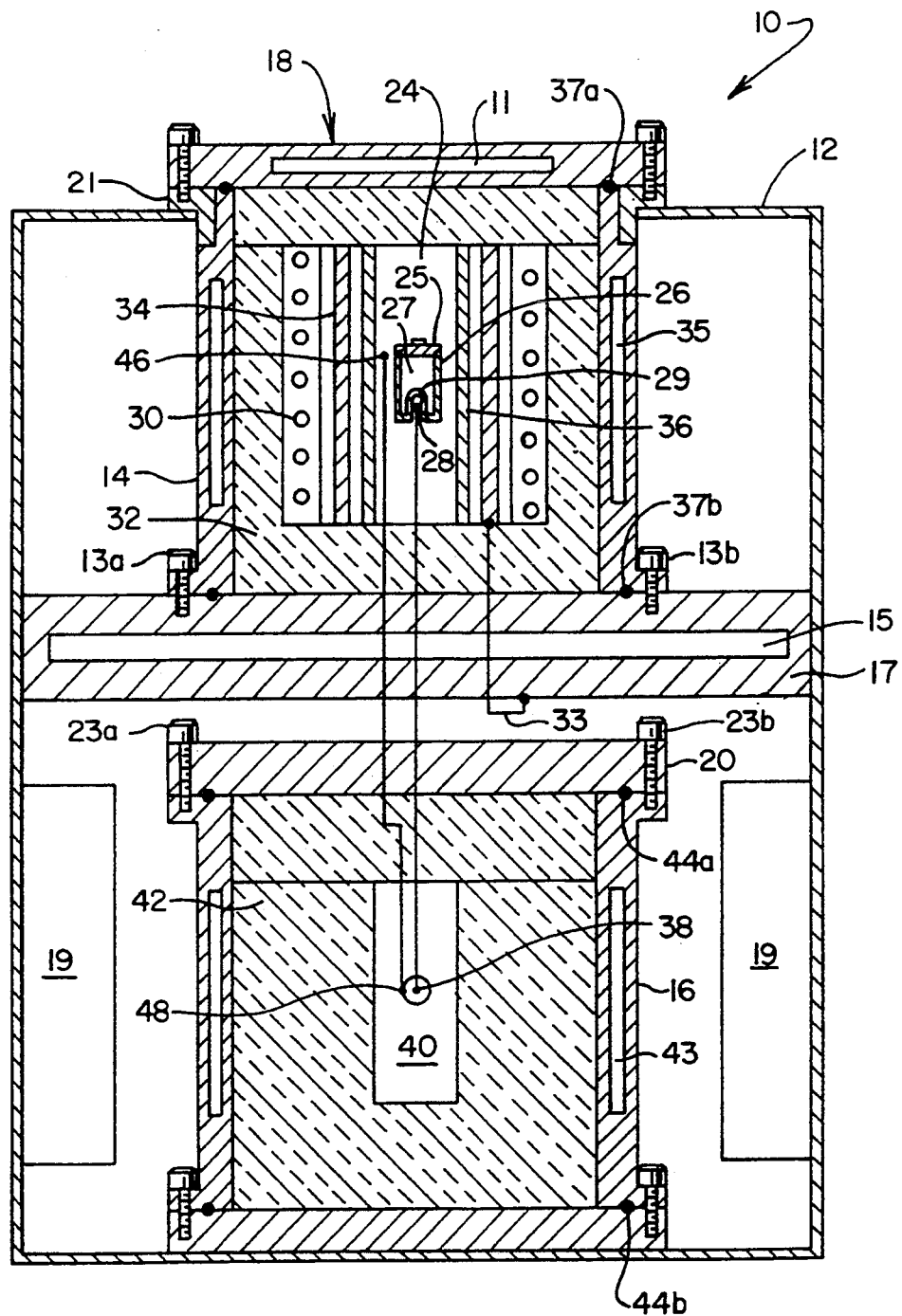
FIG. 3 is a cross-sectional view of the analyzer shown in FIG. 1 taken through reference line 3—3 of FIG. 2.

Referring to FIGS. 1, 2, and 3, the overall structure of the analyzer system of the invention is revealed generally at 10. Looking in particular to FIG. 3, analyzer 10 may be seen to be contained within a housing, 12, which houses an upper chamber, 14, and a lower chamber, 16. A base plate, 17, preferably water-cooled via an internally-disposed cavity, 15, supports upper chamber 14 which may be secured by a plurality of fasteners as represented at 13a and b. Base plate 17 also separates upper chamber 14 from lower chamber 16 which may be seen to rest on housing 12. The electronic components of analyzer 10, e.g., microprocessor, EPROM, RAM, IC boards, power supply, etc., may be located within housing 12 about lower chamber 16 as is illustrated at 19. Access to upper chamber 14 and lower chamber 16 is achieved via, respectively, an upper access plate, 18, and a lower access plate, 20. Preferably, upper access plate 18 is water-cooled via an internally-disposed cavity, 11. Lower access plate 20 is secured via a plurality of fasteners as represented at 23a and b. Looking momentarily to FIGS. 1 and 2, it may be seen that upper access plate 18 may be removably-secured via a ranged bezel, 21, to housing 12 with a plurality of knurled fasteners, 22a-f, which, preferably, are hand tightenable. Bezel 21 may be fastened to housing 12 with a plurality of screws or the like (not shown). Upper access plate 18 may be pivotally-hinged to housing 12 to allow for a 180° range of motion providing ready access to the internals of upper chamber 14.

Returning to FIG. 3, it is revealed that disposed within upper chamber 14 is an upper cavity, represented at 24, which contains a sample holder, 26, for holding the sample containing the analyte or analytes to be quantified. Although only a single sample holder is illustrated, it is to be understood that multiple sample holders may be provided for the simultaneous analysis of multiple samples. Sample holder 26, which may be provided as a crucible having a cylindrical shape and a volume of about 0.3 ml for holding a 200–500 mg sample, has a removable cover, 25, for accessing an internally-disposed chamber represented at 27, into which the sample is placed. Preferably, sample holder 26 is formed of a high temperature, refractory material such as alumina or the like and is sleeved in a metallic material such as inconel or the like to provide for electrical coupling with temperature sensors such as thermocouples, thermopiles, thermistors or the like. Crucibles suitable for use as sample holder 26 are marketed by Harrop Industries, Columbus, Ohio, under the part designation number 50-185.

To measure the thermal response of the analytes, a temperature sensor such as a high temperature thermistor, an optical sensor, a thermopile or the like is provided. For example, a sample thermocouple assembly, 28, may be disposed in thermal adjacency with sample holder 26. Depending on the resolution or millivolt output desired, sample thermocouple assembly 28 may be provided as a thermopile having a number of serially-coupled chromel-alumel, i.e., Type K, thermocouple junctions which, preferably, are potted in alumina cement or the like. For example, if crystalline silica is the analyte of interest, a 3 junction Type K thermopile with a resolution of $10^{-3°}$ C. may be employed to detect energy changes of the order of 10 millijoules (2.4 millicalories) to analyze samples containing 0.5 to 100% crystalline silica. Alternatively, if higher resolution is desired, analyzer 10 may be provided with a 21 junction Type K thermopile having a resolution approaching $10^{-4}°$ C. and the sample size may be increased to over about 2 g to give analyzer 10 a capability of detecting and determining crystalline silica concentrations down to about 0.05%. To minimize the effects of thermal parameters on the sample, sample thermocouple assembly 28 advantageously may be disposed outside rather than inside sample holder 26 via an indentation, 29, integrally-formed into sample holder 26.

Disposed about and in radiant heat transfer adjacency with sample holder 26 is a furnace, 30, for heating the sample to a temperature above the thermal transition or reaction temperature ranges of the analyte or analytes contained therein. Furnace 30 may be provided as wound wire, resistive heating elements sheathed in ceramic such as those manufactured by the Thermcraft Corporation of Winston Salem, N.C. To insulate the sample from external temperature influences, high temperature insulation, 32, preferably formed of a material having a coefficient of thermal conductivity substantially independent of temperature, may be disposed about furnace 30. Such insulation is manufactured by, for example, the Zircar Products Corporation of Florida, N.Y. under the designation SALI fiberboard. In addition, an annular jacket, 35, may be incorporated into upper chamber 14. Annular jacket 35 may be fabricated from a pair of concentric, 6061-type aluminum cylinders. Cooling water from a constant temperature source (not shown) may be circulated through jacket 35 to maintain upper chamber 14 at an essentially constant temperature, i.e., $\pm 0.01°-0.001°$ C. To isolate the sample from outside air currents, a pair of O-ring seals, 37a–b, may be employed to effect a hermetic sealing of upper chamber 14.

The hermetic sealing of upper chamber 14 also facilitates the evacuation of upper cavity 24. By evacuation of upper cavity 24 to $10^{-2}$ torr or better, internal convection currents can be suppressed to minimize convectively-induced local temperature variations within the sample. Local temperature variations within the sample can also be minimized by positioning an outer temperature equalizer, 34, having a high thermal mass in a radiant heat transfer relationship about sample holder 26 intermediate furnace 30. Outer temperature equalizer 34 may be configured as a cylindrical sleeve and formed of an electrically conductive metallic material having a high heat capacity such as Inconel ($c_p=0.109$ cal/g° C., $\lambda=0.036$ cal-cm/cm$^2$sec° C.) or the like. To diminish system noise, it is preferred that outer temperature equalizer 34 is electrically grounded to base plate 17 via a platinum wire, 33, or the like. A second, inner temperature equalizer, 36, may be placed within outer temperature equalizer 34 in conductive heat transfer adjacency with sample holder 26. Inner temperature equalizer 36 preferably is constructed of a ceramic material having a high heat capacity such as aluminum oxide ($c_p=0.22-0.29$ cal/g° C., $\lambda=0.02-0.07$ cal-cm/cm$^2$sec° C.) or the like and is configured as a cylindrical sleeve for concentric disposition within outer temperature equalizer 34.

Sample reference thermocouple assembly 28 may be seen to extend to a sample reference thermocouple assembly, 38, which, for enhanced precision, have an associated may a thermistor, 39. Reference thermistor 39 has leads 41a and 41b, and generates an absolute reference temperature signal which may be added or subtracted to the differential output of sample thermocouple assembly 28 and sample reference thermocouple assembly 38 to correct for minor variations in cold junction temperature. Reference thermocouple assembly 38 provides a zero or baseline signal with which to bias the output signal from sample reference thermocouple assembly 28. Accordingly, sample reference thermocouple assembly 38 is maintained at an essentially isothermal temperature via its disposition within a block, 40, having a high thermal mass. To insulate both block 40 and reference thermocouple assembly 38 from external temperature influences, insulation, 42, may be disposed about block 40. In addition, an annular jacket, 43, which may be fabricated from a pair of concentric, 6061-type aluminum cylinders, may be incorporated into lower chamber 16 for the circulation of cooling water therethrough. A pair of O-ring seals, 44a–b, also may be provided to effect a hermetic sealing of lower chamber 16.

Control of furnace 30 output is effected via control thermocouple assembly 46 and serially-coupled control reference thermocouple assembly 48. Preferably, control thermocouple assembly 46 is provided to be a serially-coupled thermopile disposed intermediate sample holder 26 and inner temperature equalizer 36. A control thermistor, 49, may be provided generally adjacent control thermocouple assembly 46. Similar to sample thermistor 39, control thermistor 49 has a pair of leads, 51a and 51b, for transmission of a signal corresponding to the absolute temperature within upper cavity 24. Such signal may be used as a redundant check on the differential output of control thermocouple assembly 46 and control reference thermocouple assembly 48. Control reference thermocouple assembly 48, may be disposed within block 40 in close proximity to sample reference thermocouple assembly 38. A proportional-integral-differential (PID) control system may be employed in conjunction with furnace 30 and control and control reference thermocouple assemblies 46 and 48 to maintain the sample at a preselected temperature following a ramped heating at a predetermined rate.

Looking again to FIG. 1 and also to FIG. 2, the frontal face of analyzer 10 is shown to include a microterminal, represented at 50, having a digital, alphanumeric display, 52, which may be of a liquid crystal (LCD) or a light emitting diode (LED) type. Readouts from display 52 provide visible cues as operator prompts for the inputting of operational parameters such as, for example, sample weight, and also provide messages such as operator alerts to the operational status of analyzer 10. Display 52 also may provide, upon completion of a thermal analysis run, a numerical value or quantity corresponding to the amount or concentration of the analyte having a thermally-induced, energy event contained in the sample. The amount of the analyte in the sample may be otherwise perceptibly displayed audibly, published in hardcopy or printed form, or provided in alarm or signal form as the exceeding of a preselected threshold level. A manually-actuable keyboard, 54, having predefined function keys F1–F8, shown respectively at 56a–h, and a numeric keypad, represented generally at 58, is also incorporated into microterminal 50. Operator selection of preprogrammed analyzer functions and operator inputting of operational parameters is effected via, respectively, function keys 56a–h and numeric keypad 58.

Power to furnace 30 as well as to the internal electronic components of analyzer 10 may be initiated or terminated via an on-off switch, 60, incorporated into housing 12. An indicator light, 62, may operate in conjunction with switch 60 to apprise the operator that power to analyzer 10 is being supplied. A communication or data transfer port, 64 (FIG. 2), preferably of the RS-232 type, also may be incorporated into housing 12 to provide for the uploading of data, software, firmware, or the like to an internal memory (not shown) of analyzer 10 or for the downloading of data, process signals or the like in machine readable form from the internal memory of analyzer 10 to an external memory storage device such as a personal computer or the like.

Figure 3A:
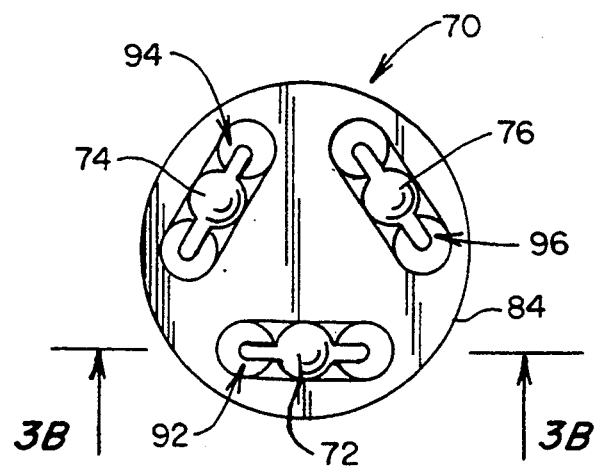
FIG. 3A is an end elevational view of a representative thermopile having serially-coupled junctions, a serially-coupled pair of which may be employed for the sample and sample reference thermocouple assemblies, and for the control and control reference thermocouple assemblies of FIG. 3.
Figure 3B:
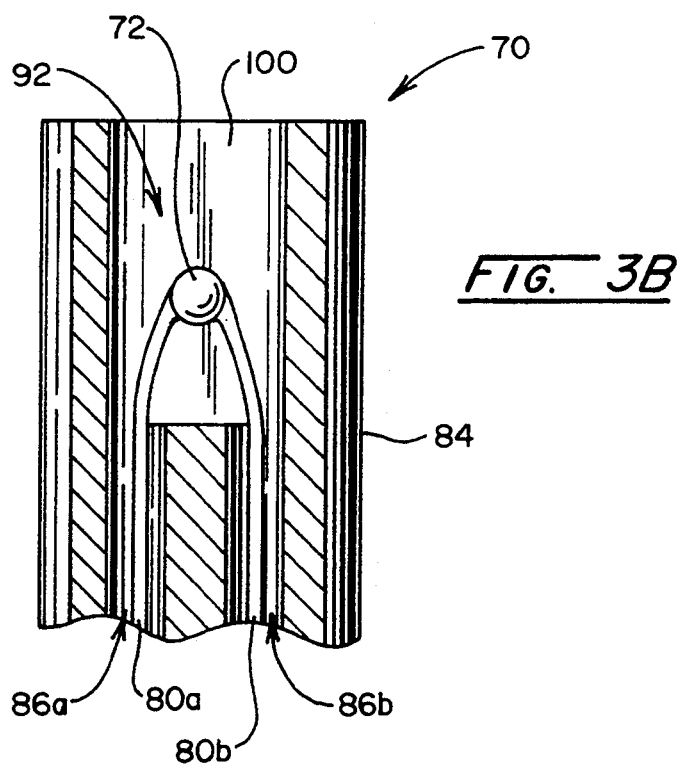
FIG. 3B is a cross-sectional view of the thermopile of FIG. 3A taken through reference line 3B—3B of FIG. 3A.

Looking momentarily to FIGS. 3A and 3B, a representative thermopile for use as sample thermocouple assembly 28, is shown generally at 70 to comprise three serially-coupled junctions, 72, 74, and 76, each of which may be of the chromel-alumel or K-type. Each of thermocouple junctions 72, 74, and 76 has a pair of leads, one pair of which is shown at 80a–b for junction 72, extending through a six-bore alumina insulator, 84, to three corresponding and similarly-configured, serially-coupled reference junctions (not shown) disposed in block 40 (FIG. 3) for forming sample reference thermocouple assembly 38 (FIG. 3). Leads 80 are insulatively received by bores 86a and 86b of insulator 84, the upper extents of which have been milled to form slots 92, 94, and 96 receiving, respectively, junctions 72, 74, and 76. As is shown at 100 for junction 72 and slot 92, slots 92, 94, and 96 may be sealed with a curable ceramic cement after the respective insertions thereinto of junctions 92, 94, and 96. Insulator 84 is provided to terminate generally at base plate 17, with the insulation of leads 80 being insulated thereafter with a polytetrafluoroethylene sheathing or the like. It will be appreciated that a similar arrangement may be employed for control thermocouple assembly 46 and control reference thermocouple assembly 48.

Alternatively, if thermistors or temperature sensors instead of thermopiles are employed for sample thermocouple assembly 28 and control thermocouple assembly 46, it will be understood that the need for sample reference thermocouple assembly 38 and control reference thermocouple 48 would be obviated as a zero or baseline signal is not needed for biasing the outputs from such sensors. Accordingly, the whole of lower chamber 16 (FIG. 3) may be eliminated when a thermistor or optical sensor is employed in lieu of a thermocouple or thermopile to measure the temperature of the sample and to effect the control of furnace 30 (FIG. 3).

Figure 4:
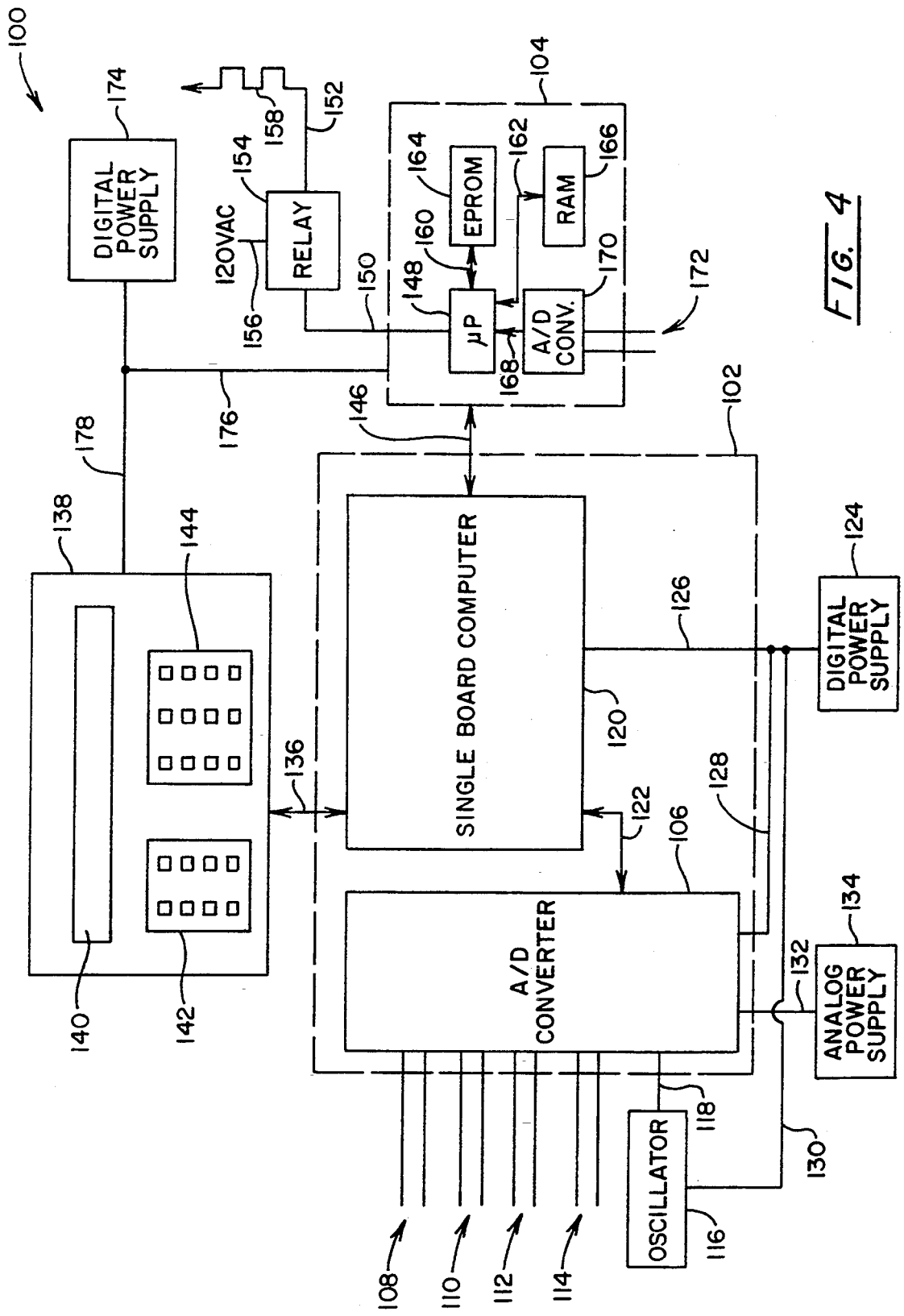
FIG. 4 is a schematic representation of a circuit for the control of the analyzer system according to the invention.

Referring to FIG. 4, an arrangement of circuitry and control components which may be employed for the operation of analyzer 10 (FIG. 1 ) is revealed in broad block schematic form at 100. These components are mounted upon two principal integrated circuit boards, a signal conditioning and microprocessor board represented by block 102 and a furnace control board represented by block 104.

Considering initially the signal conditioning and microprocessor functions represented in conjunction with block 102, an A/D converter, represented at block 106, is provided having five channels to receive analog signals from reference thermistor 39, sample thermocouple assembly 28 (FIG. 3) and reference thermocouple assembly 38 (FIG. 3) as is represented at 107, 108, 110, 112 and 114. A/D converter 106 may operate in conjunction with a multiplexer (not shown), or, in order to minimize the generation of thermal noise, a dedicated A/D converter may be provided for each thermocouple assembly input. It is preferred that A/D converter 106 is of the 24-bit type as is manufactured by, for example, the Micro Networks Corp. under the model designation 2840. Sampling frequency is, preferably, under the control of a high stability, 10 MHz oscillator as represented at block 116 and line 118. Converter 106 is also under the control of a single board computer, represented at block 120, and is coupled therewith via, for example, a 24-bit parallel I/O interface as represented at line 122. If dedicated A/D converters are provided for each thermocouple assembly, each A/D converter may be individually addressed by single board computer 120. Digital representations of the signals at channels 107, 108, 110, 112 and 114 are derived by A/D converter 106 and presented to single board computer 120 for storage in an internal memory or RAM thereof prepatory to further treatment. Power to A/D converter 106, oscillator 116, and single board computer 120 may be provided by a digital power supply, represented at block 124, via, respectively, lines 126 and 128, lines 126 and 130, and line 126. Converter 106 is powered additionally via line 132 by an analog power supply represented at block 134.

Single board computer 120 operates under an integrated microprocessor associated with integrated RAM for digital data storage and an EPROM for storage of firmware having microencoded data acquisition routines and computational algorithms. Such single board computers are manufactured by, for example, the Computer Dynamics Corporation under the designation CPU-186. Single board computer 120 receives operational inputs and parameters via an RS-232 interface as represented at line 136 from a microterminal represented at block 138. It is preferred that microterminal 138 have a 2×40 alphanumeric LCD display, represented at block 140, for the exhibition of prompts and messages relating to operational status and of process signals proportional to analyte concentration derived from acquired data which are provided to microterminal 138 by single board computer 120 via interface 136. It is also preferred that microterminal 138 have function keys, represented at block 142, for the selection of preprogrammed operations, and numeric keys, represented at block 144, for the inputting of operational parameters such as sample weight and the like. Microterminals having the desired features are manufactured by the Burr Brown Corporation under the designation CT-350. As an alternative or in addition to microterminal 138, an external computer, 145, having an integrated RAM, may be interfaced with signal conditioning and microprocessor board 102 and single board computer 120 line 147 and via another RS-232 communication port (not shown) for the entry and/or the display on a monitor or the publishing in printed form of operational parameters, data, process signals, and the like. External computer 145 also may be used as a second memory for the storage of acquired data and the like downloaded from single board computer 120.

Considering next the furnace control functions represented in conjunction with block 104, depending on which of the storm operational programs are called for by actuation of function keys 142, single board computer 120 effects a control of furnace power control board 104 via an RS-232 port and a communication line, as is represented at line 146, to achieve a desired heating or cooling schedule. A microprocessor, represented at block 148, is carried by furnace power control board 104 and is employed via lines 150 and 152 in conjunction with, preferably, a solid state relay and an associated 120 VAC supply, represented, respectively, at block 154 and line 156, to achieve, for example, a proportional-integral-derivative (PID) control over furnace 30 (FIG. 3) which is represented at 158. Microprocessor 148 functions in conventional fashion via lines 160 and 162 with, respectively, an associated EPROM, represented at block 164, and an associated RAM, represented at block 166. Feedback signals are provided to microprocessor 148 in digital form via line 168 from an associated A/D converter, represented at block 170, which receives analog inputs from control thermocouple assembly 46 (FIG. 3) as is represented at 172 and control thermistor 49 as is represent 173. Furnace control board 104 is powered by a digital power supply which may be power supply 124 or, alternatively, a second digital power supply and an associated line as is represented, respectively, at block 174 and line 176. Digital power supply 174 may also be used to power microterminal 138 via line 178.

Now considering the general operation of analyzer 10 in connection with FIGS. 1, 2, 3, and 4' in the discourse to follow, a brief description is provided of the utilization of analyzer 10 in connection with the detection and quantitative determination of a specific analyte, viz., crystalline silica, whose polymorphs exhibit thermal transitions. However, it will be appreciated that analyzer 10 may be adapted for thermal analysis of a variety of analytes having thermally-induced, energy events and associated enthalpy changes. The energy events may be, for example, crystalline phase transitions, physical phase or state transitions, or compositional changes effected by reversible or decompositional chemical reactions. Representative analytes amenable to thermal analysis are presented in Werner Smykatz-Kloss, *Differential Thermal Analysis*, pp. 96–106, Springer-Verlag (New York, 1974). Moreover, analyzer 10 may also be adapted for analysis of multiple analytes in the same sample.

In general operation, analyzer 10 quantitatively measures the amount of an analyte having a thermally-induced, energy event, such as a crystalline silica or the like which undergoes crystalline phase transitions, based on the thermal energy or enthalpy change associated with the energy event. With respect to crystalline phase transitions, in certain materials having a crystalline structure, certain crystal orientations are, thermodynamically, preferentially stable over specific temperature ranges. When, however, temperatures are reached where the crystal structure then existing becomes thermodynamically unstable, the crystal lattice endothermically or exothermically shifts to a more stable configuration. The energy consumed or liberated during this lattice shift can be measured and the amount or concentration of the analyte in the sample can be derived therefrom. For example, quartz, the thermodynamically stable form of crystalline silica at ambient temperature, exhibits a displacive, alpha-beta transition from a hexagonal to a rhombohedral structure at 573° C.±2.5° C. The phase change has an attendant energy of transition of about 1.57 cal/g. Cristobalite, a meta-stable form of crystalline silica at ambient temperature, exhibits an alpha-beta transition from a cubic to a tetragonal structure at between 170° to 275° C. with an attendant energy of transition of up to 3.3 cal/g. For a well-ordered or a well-crystallized cristobalite, this transition occurs at a more narrow temperature range of from 270° to 275° C.

Prior to analysis, the weight of the sample of interest must first be determined with a conventional analytical balance having a sensitivity of, for example, at least ±1 mg. For detection and determination of crystalline silica at concentrations of below 0.5%, however, a balance having a sensitivity of at least ±0.1 mg is required. The sample, once weighed and loaded into sample holder 26, is then placed into upper cavity 24 via upper access plate 18 which is then secured by the tightening of knurled fasteners 22a-f. Power to analyzer 10 is then supplied via actuation of switch 60 and, preferably, cooling water is recirculated through analyzer 10 until it equilibrates.

Advantageously, the operation of analyzer 10 is made automatic and is greatly simplified by the inclusion of preprogrammed function keys 56a-h. Function keys 56a-h are preprogrammed with heating or cooling routines and with data analysis routines for specific analytes. The preprogramming of function keys 56a-h may be effected through firmware embedded in the EPROM of analyzer 10. For example, function key F1, 56a, may be preprogrammed for combined crystobalite/quartz analysis and function key F2, 56b, may be preprogrammed for cristobalite analysis only. Upon actuation of the key corresponding to the analyte or analytes to be detected, the message "Enter sample wt. in mg:" is displayed on display 52 prompting the operator to enter the appropriate value via numeric keypad 58. Upon entry of the sample weight, display 52 will show the message "Heatup in progress" as well as the current sample temperature. If for example, function key F2, 56b, was pressed, furnace 30 will be powered to heat the sample at the rate of a few degrees per minute through the cristobalite data acquisition temperature region up to a temperature of 320° C. at which point the run is terminated. If, alternatively, function key F1, 56a, was pressed, furnace 30 will be powered to heat the sample through the cristobalite temperature range and then to about 640° C. at a rate of about 20–30° C./minute. At this point, a PID control system is used to ramp to and hold the sample temperature at about 700° C. Analyzer 10 will remain at this temperature to allow the system to thermally equilibrate, whereupon, power to furnace 30 will be terminated or reduced and the sample will be cooled as indicated by the displaying of a "Cooling in progress" message on display 52. When the temperature has dropped to below 470° C., data acquisition will be complete and the crystalline quartz and/or cristobalite concentrations in the sample will be displayed or otherwise published.

Considering next data acquisition, storage, and analysis, time-temperature data may be acquired from the sample by operating analyzer 10 in either a controlled linear or non-linear, i.e., PID or ramp, heating mode as the sample is heated to a temperature above the temperature range of the energy event of the analyte contained therein, or, alternatively, in a natural or controlled cooling mode as the sample is cooled after being heated to such a temperature. Irrespective of whether data is acquired in a heating or cooling mode, the millivolt or other output corresponding to the sample temperature may be taken from sample thermocouple assembly 28 at a predetermined frequency and stored as a function of time in the RAM of analyzer 10. The analysis of the time-temperature data acquired may be effected via algorithms stored as firmware in the EPROM of analyzer 10.

It is preferred that analysis of the acquired time-temperature data to derive the concentration of the analyte or analytes in the sample is effected via a method having a calorimetric sensitivity that is independent of temperature. For example, a calibration curve embedded into the firmware of analyzer 10 may be employed and compared with energy changes from measurements on unknown samples to determine the amount of analyte in the sample. To illustrate, time-temperature data may be obtained on alumina-silica reference samples containing 0%, 2%, 20%, 50%, 75% and 100%, respectively, of quartz and cristobalite standards in high purity, i.e., 99.98%, alumina. Quartz and cristobalite standards are available from the National Institute of Standards and Technology as, respectively, NBS-ICTA Standard Reference Material 760 and NBS Standard Reference Material 1879. High purity alumina is available from the Union Carbide Corporation as Linde C high purity alumina. From the time-temperature data obtained from the reference samples, a selected reference parameter may be derived whose value corresponds to the concentration of analyte in the sample. For a normalized weight or volume of sample, a reference curve may then be constructed by plotting the value of the selected reference parameter versus weight or concentration. By deriving a value of the selected reference parameter from time-temperature data obtained from a sample having an unknown concentration of analyte, the reference data may be interpolated to determine the amount of analyte in the sample. Preferably, the reference parameter is selected to be the standard deviation, $S_t$, or another statistical parameter such as the correlation coefficient of an $n^{th}$ order polynomial curve fitted to time-temperature data obtained in the vicinity of the energy event region of the analyte as the reference samples containing the preselected amounts of analyte are heated or cooled through a temperature range which includes the temperature range of the energy event of the analyte Mathematically, this may be represented by the expression:

$$\frac{C(T)S_t}{m\Delta H_t} \qquad (1)$$

where C(T) is a calibration factor which is a function of temperature, m is the mass of the sample, $\Delta H_t$ is the enthalpy change of the analyte per unit mass associated with the energy event, and $S_t$ is the standard deviation of a curve fitted around the energy event region of the time-temperature data. The curve fitting may be performed using commercially available software such as, for example, Graphics Tools Turbo C2.0 and Turbo C++1.0 Version, Revision 7.0 marketed by Quinn-Curtis Science.

The following example, which should not be construed in a limiting sense, illustrates derivation of analyte concentration from time-temperature data according to the above-referenced method.

EXAMPLE 1

A 337 mg sample of 100% NBS-ICTA quartz analyte was prepared for quantitative thermal analysis. The sample was heated in the apparatus of the invention to a temperature of about 700° C. and was held thereat under PID control for about 1 hour. The sample was then allowed to Newtonianly cool and time-temperature data in terms of sample thermocouple microvolt output was acquired and stored at 16 second intervals.

The data was divided into 5 segments: segments 1 and 2 corresponding to the pre-event thermal response of the sample; segment 3 corresponding to the energy event region thermal response of the sample: and segments 4 and 5 corresponding to the post-event thermal response of the sample. The acquired data is presented in tabular form in Table 1.

TABLE 1

| Segment | Time(sec) | Temperature(mV) |
|---|---|---|
| 1 | 16 | 78.034875 |
|  | 32 | 77.7205 |
|  | 48 | 77.4065625 |
|  | 64 | 77.0935 |
|  | 80 | 76.7813125 |
|  | 96 | 76.471875 |
|  | 112 | 76.1619375 |
|  | 128 | 75.852875 |
|  | 144 | 75.5450625 |
|  | 160 | 75.238375 |
|  | 176 | 74.93275 |
|  | 192 | 74.628625 |
|  | 208 | 74.3249375 |
|  | 224 | 74.022375 |
|  | 240 | 73.72125 |
| 2 | 16 | 74.022375 |
|  | 32 | 73.72125 |
|  | 48 | 73.421 |
|  | 64 | 73.1221875 |
|  | 80 | 72.8245625 |
|  | 96 | 72.5281875 |
|  | 112 | 72.2329375 |
|  | 128 | 71.9385625 |
|  | 144 | 71.645375 |
|  | 160 | 71.3539375 |
|  | 176 | 71.063375 |
|  | 192 | 70.773875 |
|  | 208 | 70.4860625 |
|  | 224 | 70.199375 |
|  | 240 | 69.914125 |
| 3 | 16 | 70.199375 |
|  | 32 | 69.914125 |
|  | 48 | 69.63 |
|  | 64 | 69.348125 |
|  | 80 | 69.07675 |
|  | 96 | 68.854625 |
|  | 112 | 68.6213125 |
|  | 128 | 68.343375 |
|  | 144 | 68.0544375 |
|  | 160 | 67.765125 |
|  | 176 | 67.4783125 |
|  | 192 | 67.1940625 |
|  | 208 | 66.9125625 |
|  | 224 | 66.633625 |
|  | 240 | 66.3570625 |
|  | 256 | 66.082625 |
|  | 272 | 65.8100625 |
| 4 | 16 | 66.082625 |
|  | 32 | 65.8100625 |
|  | 48 | 65.5394375 |
|  | 64 | 65.27025 |
|  | 80 | 65.0028125 |
|  | 96 | 64.7368125 |
|  | 112 | 64.4723125 |
|  | 128 | 64.209125 |
|  | 144 | 63.9473125 |
|  | 160 | 63.6868125 |
|  | 176 | 63.427625 |
|  | 192 | 63.169375 |
|  | 208 | 62.91275 |
|  | 224 | 62.6573125 |
|  | 240 | 62.4030625 |
|  | 256 | 62.14975 |
|  | 272 | 61.8974375 |
| 5 | 16 | 62.14975 |
|  | 32 | 61.8974375 |
|  | 48 | 61.646875 |
|  | 64 | 61.39725 |
|  | 80 | 61.1488125 |
|  | 96 | 60.90125 |
|  | 112 | 60.655125 |
|  | 128 | 60.4100625 |

TABLE 1-continued

| Segment | Time(sec) | Temperature(mV) |
|---|---|---|
| | 144 | 60.1660625 |
| | 160 | 59.9229375 |
| | 176 | 59.6810625 |
| | 192 | 59.4405 |
| | 208 | 59.2005625 |
| | 224 | 58.961875 |
| | 240 | 58.723875 |
| | 256 | 58.48725 |
| | 272 | 58.2516875 |
| | 288 | 58.017 |
| | 304 | 57.783375 |

For the time-temperature data in each segment, a $5^{th}$ order polynomial curve fitting was performed using commercially available software to derive a standard deviation, $S_t$. The derived $S_t$ values are presented in tabular form in Table 2.

TABLE 2

| Segment | $S_t$ ($\mu$V) |
|---|---|
| 1 | 0.375 |
| 2 | 0.133 |
| 3 | 15.417 |
| 4 | 0.085 |
| 5 | 0.119 |

Figure 5:
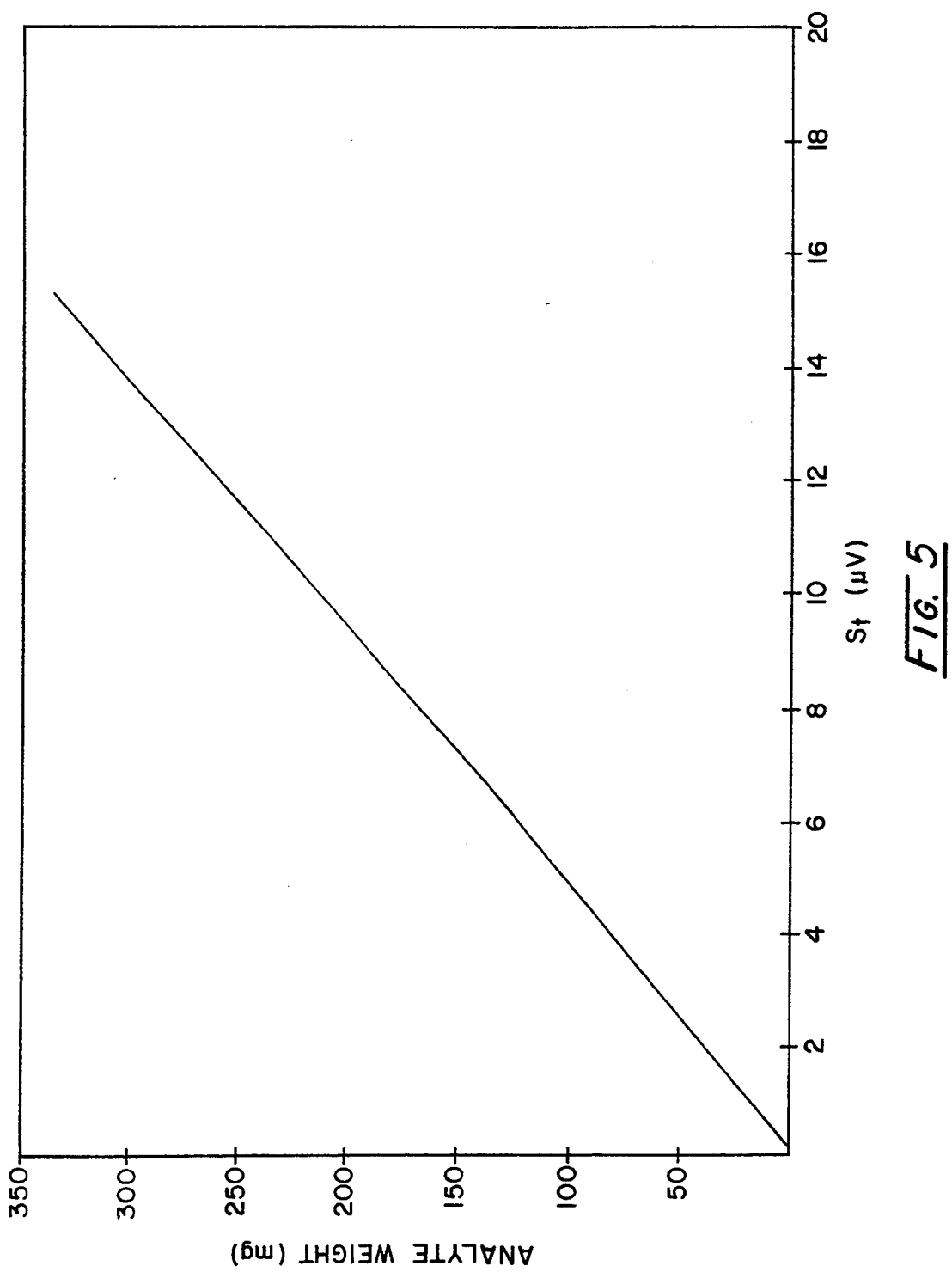
FIG. 5 is a graphical representation of a calibration curve for analysis of time-temperature data to derive analyte concentration according to one method of the invention.

The $S_t$ value for segment 3 corresponding to the energy event region thermal response of the sample is then compared with a reference curve carded by the firmware of the invention which is derived by plotting $S_t$ versus a normalized analyte weight. As FIG. 5 illustrates graphically, the value of $S_t$ exhibits a linear relationship with respect to analyte weight. Using the $S_t$ value for segment 3, the reference curve of FIG. 5 may be interpolated to derive an analyte weight. Inasmuch as the sample weight is known, analyte concentration may be derived.

As an alternative to the method illustrated in Example 1, time-temperature data also may be analyzed by dividing the resulting data set into pre-event, event, and post-event regions. A least squares analysis then is made using data contained in the pre-and the post-event segments. A residual analysis, i.e., $(y_i-y)$, is made and summed to yield the expression:

$$\sum_i (y_i - \hat{y})_{pre\text{-}event} + \sum_i (y_i - \hat{y})_{event} + \sum_i (y_i - \hat{y})_{post\text{-}event} \quad (2)$$

which is equal to a quantity related to the magnitude of the transition or reaction heat effect. The heat effect, however, is contained totally in $\Theta(Y_i-y)$ event since by definition of least squares:

$$\sum_i (y_i - \hat{y})_{pre\text{-}event} + \sum_i (y_i - \hat{y})_{post\text{-}event} = 0 \quad (3)$$

Accordingly, the concentration of analyte in the sample is obtained from the equation:

$$\% \text{ analyte} = \sum_i (y_i - \hat{y})_{event} * C(T)/m\Delta H_t \quad (4)$$

where C(T) is a calibration factor which is a function of temperature, $\Delta H_t$ is the enthalpy change of the analyte per unit mass associated with the energy event, and m is the mass of the sample.

Figure 6A:
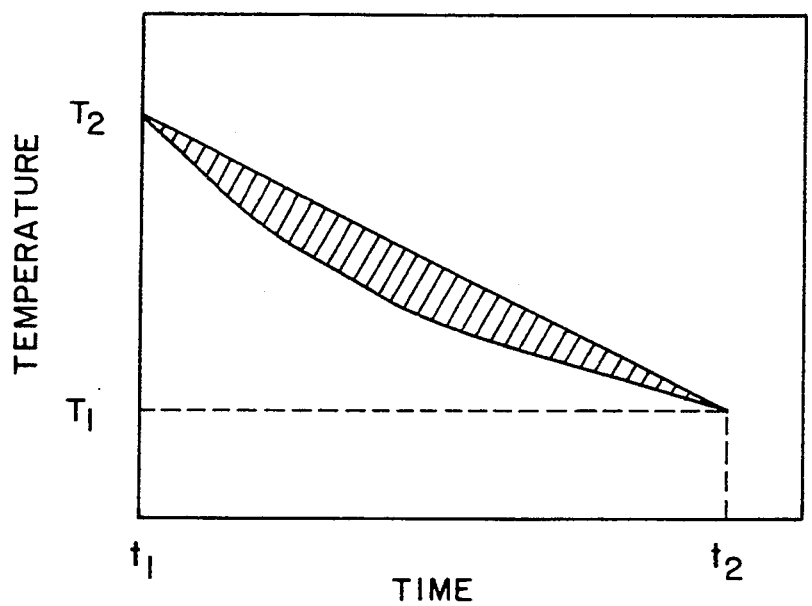
FIG. 6A is a graphical representation according to one method of the invention for analysis of time-temperature data to derive analyte concentration of the area bounded by the intersection of time-temperature data obtained in the vicinity of the energy event of the analyte and a linear segment at standard upper and lower temperatures.
Figure 6B:
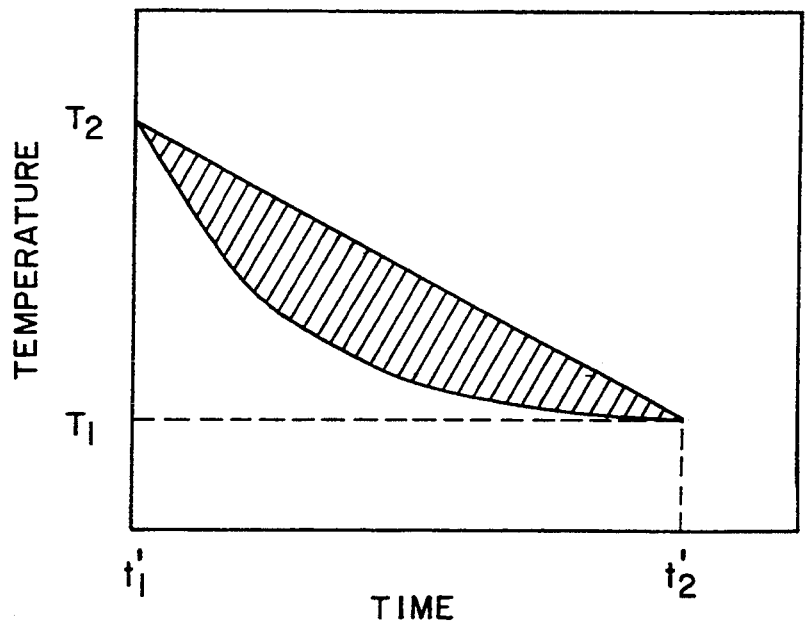
FIG. 6B is a graphical representation according to the method of FIG. 4A of the area bounded by the intersection of time-temperature data obtained from an inert sample at standard upper and lower temperatures.

Alternatively, the concentration of analyte can be obtained by fitting an $n^{th}$ order polynomial or other equation by, for example, the least squares method, to time-temperture data obtained in the vicinity of the energy event region. Again, the curve fitting may be performed using commercially available software packages. As shown graphically in FIGS. 6A and 6B, the area bounded by the intersection of this curve and a linear segment at standard upper and lower temperatures, $T_1$ and $T_2$ (FIG. 6A), when compared to time-temperature data obtained from the heating or cooling of an inert or blank sample, i.e., 0.00% analyte (FIG. 6B), is proportional to the concentration of the analyte present. Mathematically, this is given by the expression:

$$C(T) \left[ \int_{t_1}^{t_2} f(t)_{sample} dt - \int_{t'_1}^{t'_2} f(t)_{inert\ sample} dt + 1/2(T_2 - T_1)(t'_2 - t'_1 - t_2 + t_1) \right] \Big/ m\Delta H_t \quad (5)$$

where C(T) is a calibration factor which is a function of temperature, m is the mass of the sample, $\Delta H_t$ is the enthalpy change of the analyte per unit mass associated with the energy event, $f(t)_{sample}$ represents the curve corresponding to the selectively stored output signals as a function of time in the vicinity of the thermal transition or reaction temperature range of the analyte, $f(t)_{inert\ sample}$ represents the curve corresponding to the thermal response as a function of time of the inert sample, $T_2-T_1$ is the standard temperature range, $t_1$ and $t_2$ are the times corresponding, respectively, to temperatures $T_1$ and $T_2$ of the sample, and $t'_1$ and $t'_2$ are the times corresponding, respectively, to temperatures $T_1$ and $T_2$ of the inert sample. The time-temperature data for the inert sample may be obtained by running a blank in a separate run and storing the data in the RAM of the analyzer. Alternatively, pre- and post-event data in an actual run can be interpolated to derive the inert time-temperature data.

The firmware-embedded microinstructions under which a microprocessor may effect a control of the operations of analyzer 10 are represented in schematic fashion in the flowcharts shown in FIGS. 7A–D. Looking to FIG. 7A, the comprehensive program by which analyzer 10 operates in response to preprogrammed functions is revealed generally at 300. In general, the operation of the analyzer is effected via the actuation of the preprogrammed function keys, 56a–h, as represented at blocks 330 and 340. For illustrative purposes, only function keys F1-F3, 56a–c, are described as having preprogrammed functions directed to the thermal analysis of quartz and cristobalite, F1, the thermal analysis of cristobalite only, F2, and the downloading of acquired time-temperature data to an external memory storage such as a personal computer via communication port 64, F3. However, it may be understood that the remaining function keys, F4–F8, 56d–h, or any additional number thereof can be preprogrammed with additional features to extend the capability of analyzer 10. For example, additional keys can be preprogrammed with heating, cooling, and data analysis routines for the analysis of other analytes. Also, if additional hardware is provided, function keys can be assigned for the simultaneous analysis of more than one sample.

Considering now the operational steps of program 300, entry into the program is represented at block 310. Block 310 leads to a start-up procedure, represented at 320 wherein conventional initialization procedures are carded out. Following initialization, a query is made as represented at block 330 to determine whether function key F1, 56a, was actuated to call for a combined cristobalite-quartz analysis. In the event that the query at block 330 is in the affirmative, the program progresses as represented at line 332 to the steps illustrated in FIGS. 7B and 7C. In the event that the query at block 330 is in the negative, the program proceeds to block 340 where another query is made to determine if function key F2, 56b, was actuated to call for cristobalite analysis only. If the query at block 340 is in the affirmative, the program progresses as represented at line 342 to the steps illustrated in FIG. 7D. If the query at block 340 is in the negative, the program is terminated via line 344 leading to the end node represented at block 360.

Figure 7C:
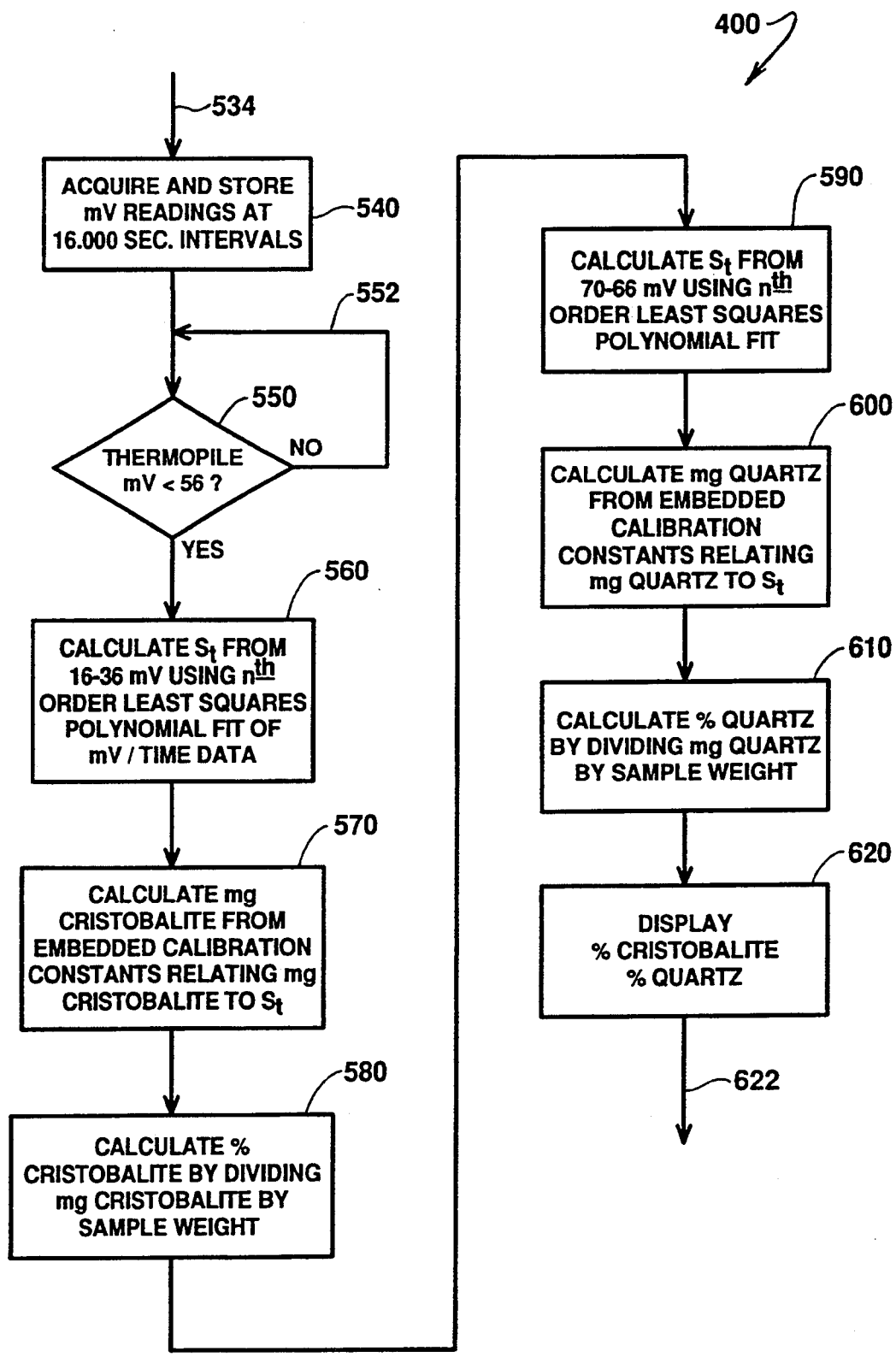

Looking to FIGS. 7B and 7C, in the event that the query at block 330 of FIG. 7A is in the affirmative, the quartz-cristobalite subroutine represented at block 400 of FIG. 7B is entered into via line 332. Line 332 leads to the operator instruction at display 52 and represented at block 410 requesting entry of the sample weight. Upon entry of the sample weight by the operator from keypad 58, the program proceeds to power up furnace 30 at, for example, a rate of 1% per minute as represented at block 420 in order to heat the sample through its cristobalite transition temperature. Following commencement of furnace 30 heat-up, a query is made as represented at block 430 to determine whether the output from the sample thermocouple assembly is greater than, for example, 12.5 mV. In the event that it is not, a loop is entered as represented by loop line 432. Once the specified thermocouple output is reached and the query at block 430 is in the affirmative, cristobalite time-temperature dam in the form of millivolt readings are acquired through a predetermined temperature range and stored, for example, at a preselected 16 second interval as represented at block 440. As is represented at query block 450 and loop line 452, cristobalite data acquisition continues until control thermocouple assembly 46 indicates a temperature greater than, for example, 320° C. Once this condition is reached and the query represented at block 450 is in the affirmative, cristobalite data acquisition is discontinued and furnace power is increased to, for example, 70%, as is represented at block 460. As the query represented at block 470 and loop line 472 represents, sample heat-up is continued to near the quartz transition temperature. When control thermocouple assembly 46 indicates, for example, a temperature of greater than 640° C., the condition posed at block 470 is satisfied and, as is represented at block 480, furnace 30 power may be ramped 2°0 C./min under PID control with an initial integral or reset action set to 35% of maximum furnace 30 power. From block 480, subroutine 400 proceeds to the query represented at block 490. As represented by loop line 492, a loop is entered until control thermocouple assembly 46 indicates a temperature greater than, for example, 700° C. When this condition is satisfied, a timer is reset to zero, a control setpoint is defined at 700° C., and PID control is maintained as is represented at block 500. As is represented at block 510 and by loop line 512, sample temperature is held at 700° C. over a predetermined time interval of, for example, one hour. After sample heat-up through the quartz transition temperature, furnace power is terminated as is represented at block 520. From block 520, the query represented at block 530 and by loop line 532 is entered to allow the sample to cool until a sample thermocouple assembly 28 output of less than, for example, 80 mV is reached. Continuing to FIG. 7C via line 534, when the condition of block 530 is satisfied, as is represented at block 540, time-temperature data is acquired and stored at, for example, 16 second intervals, as the sample cools through its quartz transition temperature. Data acquisition is continued through a predefined temperature range until the query represented at block 550 and by loop line 552 is satisfied when the output from sample thermocouple assembly 28 is less than, for example, 56 mV.

From block 550, routine 400 then proceeds, as is represented at block 560, to calculate the standard deviation, $S_t$, in the cristobalite transition region of from about 16–36 mV using, for example, an $n^{th}$ order least squares polynomial fit of the acquired time-temperature, i.e., millivolt, data. As is represented at block 570, from the calculated $S_t$, the weight of cristobalite corresponding therewith may be found using the embedded reference or calibration constants relating cristobalite weight to $S_t$. From block 570, subroutine 400 continues to block 580 where the concentration of cristobalite is derived by dividing the cristobalite weight from block 570 by the sample weight from block 410. Subroutine 400 then progresses to an analysis of the quartz data which was acquired at block 440. As is represented at block 590, the standard deviation, $S_t$, in the quartz transition region of from about 70–66 mV is calculated as is represented at block using, for example, an $n^{th}$ order least squares polynomial fit of the acquired time-temperature, i.e., millivolt, data. Continuing to block 600, from the value of $S_t$ derived in block 590, the weight of quartz corresponding therewith may be found using the embedded reference or calibration constants relating quartz weight to $S_t$. From block 600, the program continues to block 610 where the concentration of quartz is derived by dividing the quartz weight from block 600 by the sample weight from block 410. As is represented at block 620, the concentration of cristobalite derived in block 580 and the concentration of quartz derived in block 610 may be displayed as a percentages on display 52. Routine 400 then returns to main program 300 via line 622.

Looking to FIG. 7D, in the event that the query at block 340 of FIG. 7A is in the affirmative, the cristobalite subroutine represented at 700 is entered into via line 342. Line 342 leads to the operator instruction represented at block 710 requesting entry of the sample weight. Upon entry of the sample weight by the operator, the program proceeds to power up furnace 30 at, for example, a rate of 1% per minute as represented at block 720 in order to heat the sample through its cristobalite transition temperature. Following commencement of furnace 30 heat-up, a query is made as represented at block 730 to determine whether the output from sample thermocouple assembly is greater than, for example, 12.5 mV. In the event that it has not, a loop is entered as represented by loop line 732. Once the specified thermocouple output is reached and the query at block 730 is in the affirmative, cristobalite time-temperature data in the form of millivolt readings are acquired through a predetermined temperature range and stored, for example, at a preselected 16 second interval as represented at block 740. As is represented at query block 750 and loop line 752, cristobalite data acquisition continues until control thermocouple assembly 46 indicates a temperature greater than, for example, 320° C. Once this condition is reached and the query represented at block 750 is in the affirmative, cristobalite data acquisition is discontinued and furnace power is discontinued as is represented at block 760. From block 760, the program then proceeds, as is represented at block 780, to calculate the standard deviation, $S_t$, in the cristobalite transition region of from about 16–36 mV using, for example, an $n^{th}$ order least squares polynomial fit of the acquired time-temperature, i.e., millivolt, data. As is represented at block 790, from the calculated $S_t$, the weight of cristobalite corresponding therewith may be found using the embedded reference or calibration constants relating cristobalite weight to $S_t$. From block 790, the program continues to block 800 where the concentration of cristobalite is derived by dividing the cristobalite weight from block 790 by the sample weight from block 710. As is represented at block 810, the concentration of cristobalite derived in block 800 may be displayed as a percentage via display 52. Routine 700 then returns to main program 300 via line 812.

Returning to program 300 and to FIG. 7A, line 812 from routine 700 and line 622 from routine 400 lead to the query represented at block 370. For both routine 700 and routine 400, a query is made at block 370 to determine whether function key F3, 56c, was actuated to call for the downloading of the acquired time-temperature data to an external memory storage via communication port 64. In the event that the query at block 370 is in the affirmative, data is downloaded as represented at block and the program is terminated at node 360. In the event that the query at block 370 is in the negative, program 300 proceeds directly to termination at node 360.

Since certain changes may be made in the above-described apparatus and method without departing from the scope of the invention herein involved, it is intended that all matter contained in the description thereof or shown in the accompanying drawings shall be interpreted as illustrative and not in a limiting sense.

I claim:

1. A system for determining the amount in at least one sample of at least one analyte having a thermally-induced, energy event and an associated enthalpy change, comprising:

sensor means for providing output signals of amplitude corresponding to the temperature of said sample;

data input means manually actuable for deriving select function signals and operational parameter inputs;

a first closable chamber for receiving the sample;

heating means disposed within said first chamber in heat transfer adjacency with said sample and responsive to control signals submitted thereto for heating or cooling said sample at a preselected rate;

an oscillator for deriving oscillator sampling signals at a predetermined frequency;

converter means responsive to said output signals from said sensor means for generating sample digital signals corresponding therewith, and to said oscillator sampling signals from said oscillator for generating oscillator sampling digital signals corresponding therewith;

first memory means for selectively storing with associated time signals said sample digital signals received from said converter means, said sample digital signals and associated time signals corresponding to the thermal response of said sample; and processing means responsive to a first select function signal and said operational parameter inputs from said data input means for deriving said control signals and effecting the submittal thereof to said heating means, for effecting responsive to said oscillator sampling digital signals the selective storage by said first memory means of said sample digital signals and said associated time signals over a predetermined temperature range which includes the temperature range of said energy event of said analyte, for retrieving the selectively stored sample digital signals and associated time signals from said first memory means, and for deriving process signals proportional to the amount of said analyte in said sample from the retrieved sample digital signals and time signals.

2. The system of claim 1 wherein said data input means is a keypad.

3. The system of claim 1 wherein said data input means is a computer.

4. The system of claim 1 wherein said sensor means comprises a thermistor.

5. The system of claim 1 wherein said sensor means comprises an optical sensor.

6. The system of claim 1 wherein said sensor means comprises;

sample thermocouple means disposed in thermal adjacency with said sample; and sample reference thermocouple means maintained substantially isothermally and serially coupled to said sample thermocouple means for deriving therewith said output signals.

7. The system of claim 6 further comprising a second closable chamber for retaining said sample reference thermocouple means.

8. The system of claim 7 wherein said second closable chamber is configured for sealing said sample reference thermocouple means.

9. The system of claim 7 wherein said second closable chamber is water-cooled.

10. The system of claim 6 further comprising a block means exhibiting a high thermal mass disposed in conductive heat transfer adjacency about said sample reference thermocouple means for maintaining said sample reference thermocouple means essentially isothermally.

11. The system of claim 6 further comprising insulation disposed about said sample reference thermocouple means in heat transfer adjacency therewith.

12. The system of claim 6 wherein said sample thermocouple means and said sample reference thermocouple means are thermopiles having serially-coupled junctions.

13. The system of claim 6 further comprising a reference thermistor disposed adjacent said sample reference thermocouple means for generating an absolute reference temperature signal, said processing means also being responsive to said absolute reference temperature signal to correct said sample digital signals in conformance therewith.

14. The system of claim 1 further comprising a second memory means for storing the sample digital signals and the associated time signals selectively stored by said first memory means, said processing means being responsive to a second function signal from said data input means for effecting the submittal of the selectively stored digital signals retrieved from said first memory means to said second memory means.

15. The system of claim 14 wherein said second memory means is a personal computer.

16. The system of claim 1 wherein said first closable chamber is configured for hermetically sealing said sample.

17. The system of claim 16 wherein said first closable chamber is evacuatable.

18. The system of claim 1 further comprising:
a sample holder within which said sample is disposed; and
a first temperature equalizing assembly disposed intermediate and in radiant heat transfer adjacency with said sample holder and said heating means.

19. The system of claim 18 wherein said first temperature equalizing assembly comprises a cylindrical sleeve formed of a material exhibiting a high thermal mass.

20. The system of claim 19 wherein said first temperature equalizing assembly is formed of inconel.

21. The system of claim 18 wherein said first temperature equalizing assembly is electrically conductive and electrically grounded.

22. The system of claim 19 further comprising a second temperature equalizing assembly disposed intermediate and in radiant heat transfer adjacency with said sample holder and said first temperature equalizing assembly.

23. The system of claim 22 wherein said second temperature equalizing assembly comprises a cylindrical sleeve formed of a material exhibiting a high thermal mass disposed concentric with said first temperature equalizing assembly.

24. The system of claim 22 wherein said second temperature equalizing assembly is formed of alumina.

25. The system of claim 1 further comprising high temperature insulation disposed about said means, said high temperature insulation having a coefficient of thermal conductivity substantially independent of temperature.

26. The system of claim 1 wherein said first closable chamber is water-cooled.

27. The system of claim 1 further comprising a perceptible means responsive to said process signals for displaying the amount of said analyte in said sample, said processing means responsive to a select function signal for effecting the submittal of said process signals to said perceptible means.

28. The system of claim 27 wherein said perceptible means comprises a visually perceptible display for displaying characters representing the amount of said analyte in said sample.

29. The system of claim 28 wherein said visually perceptible display comprises a multi-segmented, character-defining light emitting diode means for visually displaying characters representing the amount of said analyte in said sample.

30. The system of claim 1 further comprising:
control thermocouple means disposed in heat transfer adjacency with said heating means;
control reference thermocouple means maintained essentially isothermally and serially coupled to said control thermocouple means for deriving output signals therewith, said processing means also being responsive to the output signals generated by the serially-coupled control and control reference thermocouple means for deriving said control signals and effecting the submittal thereof to said heating means.

31. The system of claim 30 wherein said control thermocouple means and said control reference thermocouple means are thermopiles having serially-coupled junctions.

32. The system of claim 30 further comprising a control thermistor disposed generally adjacent said control thermocouple means for generating an absolute control temperature signal, said processing means also being responsive to said absolute control temperature signal to compare the output signals generated by the serially-coupled control and control reference thermocouple means therewith.

33. The system of claim 1 wherein said processing means is responsive to a second select function signal for storing reference data corresponding to a preselected reference parameter, said process signals being derived by determining the value of said reference parameter for the retrieved sample digital signals and interpolating said reference data to determine the amount of said analyte corresponding therewith.

34. The system of claim 33 wherein said reference parameter is provided to be the standard deviation of an $n^{th}$ order polynomial corresponding to the thermal responses as functions of time of preselected amounts of said analyte which are heated or cooled through the temperature range of said energy event of said analyte.

35. The system of claim 33 wherein said reference parameter is provided to be the correlation coefficient of an $n^{th}$ order polynomial corresponding to the thermal responses as functions of time of preselected amounts of said analyte which are heated or cooled through the temperature range of said energy event of said analyte.

36. The system of claim 1 wherein said process signals arc derived by a least squares analysis of the selectively-stored sample digital signals corresponding to the thermal response of said sample before and after said energy event of said analyte, and a residual analysis of the selectively-stored sample digital signals corresponding to the thermal response of said sample over the predetermined temperature range which includes the temperature range of said energy event.

37. A system for determining the amount in at least one sample of at least one analyte having a thermally-induced, energy event and an associated enthalpy change, comprising:
sensor means for providing output signals of amplitude corresponding to the temperature of said sample;
data input means manually actuable for deriving select function signals and operational parameter inputs;
a first closable chamber for receiving the sample;
heating means disposed within said first chamber in heat transfer adjacency with said sample and responsive to control signals submitted thereto for heating or cooling said sample at a preselected rate;

converter means responsive to said output signals from said sensor means for generating sample digital signals corresponding therewith;

first memory means for selectively storing with associated time signals said sample digital signals received from said converter means; and processing means responsive to a first select function signal and said operational parameter inputs from said data input means for deriving said control signals and effecting the submittal thereof to said heating means, for effecting the selective storage by said first memory means of said sample digital signals and associated time signals over a predetermined temperature range which includes the temperature range of said energy event of said analyte, for retrieving the selectively stored sample digital signals and associated time signals from said first memory means, and for deriving process signals proportional to the amount of said analyte in said sample from the retrieved sample digital signals and associated time signals, said processing means including integration means for integrating a first region defined by a first curve corresponding to the selectively stored sample digital signals in the vicinity of said energy event of said analyte and a select lower bound thereof, for integrating a second region defined by the intersection of a second curve and a select lower bound thereof corresponding to the thermal response as a function of time over the preselected temperature range of a preselected inert reference sample, and for determining the difference in area between said first and said second region to derive said process signals.

38. The system of claim 37 wherein said first curve corresponding to the selectively stored sample digital signals in the vicinity of said energy event of said analyte is derived by fitting an $n^{th}$ order polynomial to the selectively stored sample digital signals.

39. The system of claim 38 wherein the $n^{th}$ order polynomial fitted to the selectively stored sample digital signals is derived by the least squares method.

40. The system of claim 38 wherein said second curve is derived from inert reference sample digital signals and associated time signals stored in said first memory means, said inert reference sample digital signals and associated time signals corresponding to the thermal response as a function of time over the preselected temperature range of said inert reference sample.

41. The system of claim 40 wherein said second curve corresponding to the thermal response of said inert reference sample is derived by fitting an $n^{th}$ order polynomial to the inert reference sample digital signals stored in said first memory means.

42. The system of claim 41 wherein the $n^{th}$ order polynomial fitted to the inert reference sample digital signals stored in said first memory means is derived by the least squares method.

43. The system of claim 38 wherein said integration means includes interpolating means for interpolating the selectively stored sample digital signals before and after said energy event of said analyte to derive said second curve corresponding to the thermal response of said inert reference sample.

* * * * *